United States Patent [19]
Dory

[11] Patent Number: 5,431,621
[45] Date of Patent: Jul. 11, 1995

[54] PROCESS AND DEVICE OF AN ANATOMIC ANOMALY BY MEANS OF ELASTIC WAVES, WITH TRACKING OF THE TARGET AND AUTOMATIC TRIGGERING OF THE SHOOTINGS

[75] Inventor: Jacques Dory, Coupvray, France

[73] Assignee: EDAP International, France

[21] Appl. No.: 233,712

[22] Filed: May 15, 1991

Related U.S. Application Data

[60] Continuation of Ser. No. 250,479, Sep. 28, 1988, abandoned, which is a continuation-in-part of Ser. No. 37,369, Apr. 13, 1987, abandoned, which is a division of Ser. No. 728,905, Apr. 30, 1985, Pat. No. 4,658,858, which is a continuation-in-part of Ser. No. 674,889, Nov. 26, 1984, Pat. No. 4,617,931.

[30] Foreign Application Priority Data

Oct. 2, 1987 [FR] France .................. 87 13618

[51] Int. Cl.$^6$ .............. A61B 8/00; A61B 17/22
[52] U.S. Cl. ........................... 601/2; 601/4; 128/660.03; 128/660.05; 128/660.07; 128/660.08; 128/600.09; 367/96
[58] Field of Search ......... 128/660.01, 660.03, 128/660.05, 660.07, 660.08, 660.09; 601/2, 3, 4; 367/96

[56] References Cited

U.S. PATENT DOCUMENTS

| | | | |
|---|---|---|---|
| 3,735,755 | 5/1973 | Eggleton et al. | 128/24 A |
| 4,617,931 | 10/1986 | Dory | 128/304 |
| 4,620,545 | 11/1986 | Shene et al. | 128/24 A |
| 4,620,546 | 11/1986 | Aida et al. | 128/24 A |
| 4,658,828 | 4/1987 | Dory | 128/660.03 |
| 4,669,483 | 6/1987 | Hepp et al. | 128/660.03 |
| 4,745,920 | 5/1988 | Forssmann et al. | 128/328 |
| 4,757,820 | 7/1988 | Itoh | 128/660.03 |
| 4,763,652 | 8/1988 | Brisson et al. | 128/24 A |
| 4,771,787 | 9/1988 | Wurster et al. | 128/660.03 |
| 4,821,729 | 4/1989 | Makofski et al. | 128/660.03 |
| 4,829,986 | 5/1989 | Eichler et al. | 128/24 A |
| 4,844,079 | 7/1989 | Naser et al. | 128/660.03 |

*Primary Examiner*—Krista M. Zele
*Attorney, Agent, or Firm*—Welsh & Katz Ltd.

[57] ABSTRACT

A Process and device of location and destruction of an anatomic target includes the periodic emission of a focused treatment beam of elastic waves and an echographic image of the target formed in real time during the treatment period by means of an ultrasonic auxiliary beam carrying out a scanning substantially centered in a symmetry plane of the focused treatment beam. Also displayed superimposed on the target image is a mark showing the theoretical position of the focal point of the treatment beam. Selection of the image forming echoes reflected from the target as a function of the coordinates of the region of impact of the auxiliary beam with respect to the echographic source is effected and the treatment and auxiliary sources are simultaneously displaced under the control of signals derived from the selected echoes until the coincidence between the image of the mark and the image of the target object is reached where the treatment beam emission is then triggered.

6 Claims, 2 Drawing Sheets

PROCESS AND DEVICE OF AN ANATOMIC ANOMALY BY MEANS OF ELASTIC WAVES, WITH TRACKING OF THE TARGET AND AUTOMATIC TRIGGERING OF THE SHOOTINGS

This application is a continuation of Ser. No. 07/250,479 filed on Sep. 28, 1988 and abandoned which is a continuation-in-part of Ser. No. 07/037,369 filed on Apr. 13, 1987 and abandoned which is a divisional of Ser. No. 06/728,905 filed Apr. 30, 1985 and issued as U.S. Pat. No. 4,658,858 which was subsequently reissued as RE 33,590 on May 21, 1991, where Ser. No. 06/728,905 was a continuation-in-part of Ser. No. 06/674,889 filed Nov. 26, 1984 and issued as U.S. Pat. No. 4,617,931 and upon which Applicant claims benefit of the filing dates of U.S. Pat. No. 4,617,931 which claims the benefit of French Application 83 20041 filed on Dec. 14, 1983.

BACKGROUND OF THE INVENTION

1. Field of the Invention

In extra-corporal lithotripsy, hyperthermy or in treatment of degenerated cells by means of elastic waves, locating the target, presents difficulties: through the high power elastic waves which effect the destruction of the target, either by heating or by imparting mechanical stresses can be easily focused by means of an acoustic system comprising a lens, a reflector or an emissive surface having a focus, the unavoidable differences in propagation speed of the elastic waves between the coupling media and the patient's body, which is of non homogeneous structure, give rise to refraction phenomena the effect of which is that the real focus position inside the body cannot be accurately determined from the knowledge of the theoretical position, such as defined by the acoustic system.

2. Description of the Prior Art

Several processes have been proposed for the location of the target. Those using X-rays have the drawback, besides their destructive character, are not able to show, for instance the location of certain gall-stones which are transparent to the X-rays. Ultrasonic echography is free of these drawbacks but presents at first sight a certain number of difficulties: the target can be reached only through a more or less narrow acoustic window; the destructive signals have a frequency too low for the echography and a power too high at least for extra-corporal lithotripsy.

If the destruction signals are produced by a piezoelectric ceramic, the ceramic has dimensions too large to be displaced at "real time" scanning rates, and anyway the focus must remain fixed during the treatment periods, thus excluding the use of the power transducer for the location during the treatment itself. The processes using an echography of the A type and measurements or determination effected without visual display are not sufficiently reliable for assuring the location control during the shootings, whereas this control is essential, since the target, specially when it concerns a stone, will move at the rate of the breathing and can even shift suddenly. In hyperthermy, a "real time" control is particularly essential and must be accurate, in order to avoid the destruction of healthy cells.

In the U.S. Pat. No. 4,617,931 filed on 26 Nov. 1984, the Applicant has described a visual location process which consists mainly of a real time echographic image formed of the target between the shootings during the treatment period, by means of an ultrasonic auxiliary beam, carrying out a scanning centered preferably in a symmetry plane of the main focused beam of destruction, wherein the plane of image formation thus passes through the main beam focus. Visual display of the target includes a mark showing the theoretical position of the focus, which is brought by the operator into coincidence with the image of the target by moving as a whole the two sources emitting the respective beams. The specification of said US patent is incorporated in this specification by way of reference as essential material thereof.

This process enables a permanent and accurate visual control of the location of the target during the shootings. The above-mentioned patent describes also an important improvement by which it can be verified, at any given moment that the ultrasonic destructive energy is effectively transmitted to the focus and that it is homogeneously distributed on the whole of the focal spot. To this effect, it discloses the use of the main source as an emitter of a fixed echographic beam, and of the auxiliary source as a receiver of the echoes formed by a reflection of said fixed beam, thus forming an image of the corresponding focal spot, by carrying out a scanning with the auxiliary source.

SUMMARY OF THE INVENTION

The invention has as its objects, improvements to the location and treatment methods, and particularly improvements to those of the above-mentioned patent.

A first improvement enables the target tracking and the automatic triggering of the shootings when the target is reached.

According to the invention, this result is obtained by the selection of the echoes forming the target image as a function of the coordinates of the region of impact of the echographic beam against the target, with respect to the echographic source, by controlling the displacement of the two sources as a whole be means of signals derived from the selected echoes, until coincidence is reached and by the automatic triggering of the shootings when this coincidence is achieved.

According to a preferred embodiment, the echographic scanning is a sectoral scanning of the B type carried out successively in two orthogonal planes and the echo selection is done, in each plane, in relation to the angular position of the echographic beam with respect to the scanning axis and to the distance of the impact region of the echographic scanning beam to the echographic source.

A second improvement consists in utilizing simultaneously the main source as an emitter of a fixed echographic beam, and the auxiliary source as an emitter of a scanning echographic beam, the auxiliary source being then used as a receiver of the echoes formed by reflection of the two beams, thus enabling the simultaneous formation of a target image and of a focal spot image superimposed in overbrightness to the target image.

The invention further provides devices for the implementation of the above-mentioned methods.

BRIEF DESCRIPTION OF THE DRAWINGS

The invention will be better understood from the following description with reference to the drawings in which.

DESCRIPTION OF A PREFERRED EMBODIMENT

Figure 1:
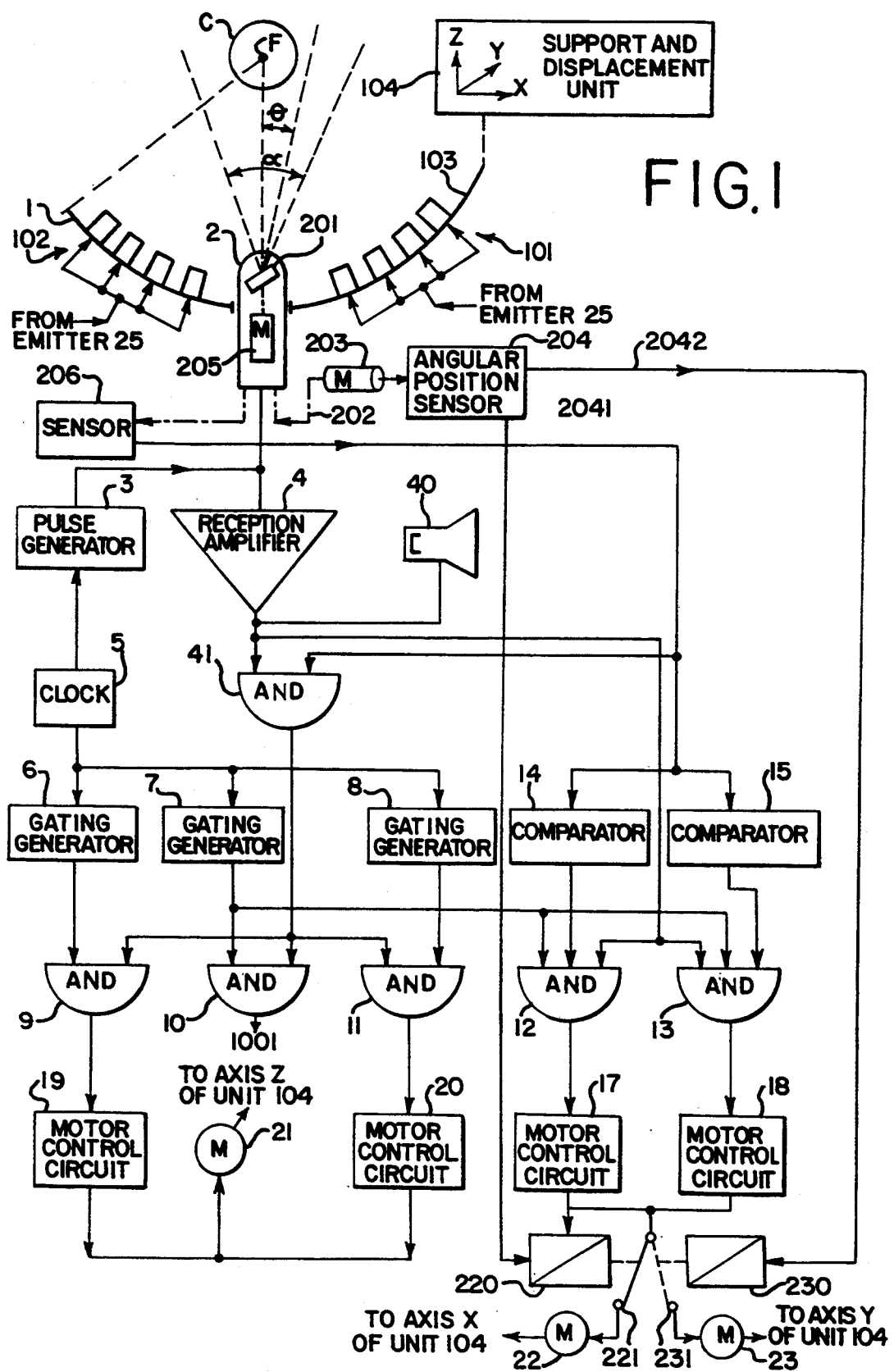
FIG. 1 is a block diagram of a location and treatment device with target tracking according to a preferred embodiment.

FIG. 1 represents diagrammatically a power ultrasonic wave generator 1 comprising several groups of piezoelectric transducers such as 101, 102 mounted on a portion of a spherical cap 103 and producing a fixed conical beam focused at F. The focus F has to be brought in coincidence with a target C.

A sectoral scanning echographic probe 2 goes through a hole provided at the top of cap 103 and is positioned along the axis of the cap. It comprises an oscillating emitter and receiver transducer 201 which is oscillated by motor 205 and emits, when excited by an electric pulse emitter 3 synchronized by a clock 5, (FIG. 3) a narrow ultrasonic echographic beam scanning an angular sector $\alpha$, the axis of symmetry of which merges with that of the cap. The mounting of the probe 2 is such that it can rotate around its own axis of symmetry, while being mechanically connected to generator 1. The orthogonal displacements of generator 1 are controlled, as disclosed in U.S. Pat. No. 4,617,931, by a support and displacement device 104 allowing it to move along three orthogonal axes X, Y, and Z, when actuated by three motors 21 (displacement according to the cap axis or vertical Z), 22 (displacement in the plane of FIG. 1, or longitudinal X) and 23 (displacement perpendicular to the plane of FIG. 1 or transversal Y). As illustrated in FIG. 1, motor 22 is connected to an input 104x of device 104 for control of longitudinal displacements; motor 23 is connected to an input 104y of device 104 for control of transversal displacements and motor 27 is connected to an input 104z of device 104 for control of vertical displacement. At periodic time intervals, the probe 2 is on the other hand driven in rotation around its axis, in such a way as to shift, for instance in less than a second, from a first position in which the echographic beam scans the plane of the figure, to a second position in which it scans an orthogonal plane. This periodical angular displacement is automatically controlled by a motor 203 through a transmission mechanism shown symbolically by a double-dashed line 202. A sensor device 204, which can include two end of travel switches, supplies a signal on one of its outputs 2041 or 2042, according to whether the scanning is carried out in the figure plane or in a perpendicular plane.

The echoes received by probe 2 are amplified by a reception amplifier 4 and are then transmitted through an AND gate 41, to AND gates 9, 10, and 11, at the time when a signal indicating that the echographic beam is substantially centered on the probe axis ($\theta = E$) is supplied to the gate 41 by a sensor device 206 which continuously measures the angular position Q of the transducer 201. When echoes are received, i.e. when the target is inside the echographic beam, the echoes are transmitted to a first input of the AND gates 12 and 13, the inputs of which are also connected to the output of the amplifier 4.

The AND gates 9, 10 and 11 are respectively opened by the signals applied to them by gating pulse generators 6, 7 and 8, provided respectively, as it will be explained further on, to carry out the selection of the echoes, coming from reflective surfaces located on the device axis, respectively beyond the focus F, on the focus itself and on the other side of the focus. These gating pulses, of predetermined duration, are initiated by the synchronization pulses formed by the clock 5.

Figure 2:
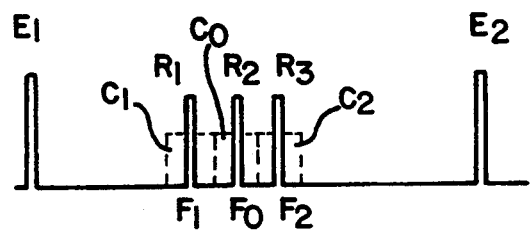
FIG. 2 is a diagram of said embodiment of FIG. 1 depicting pulses and pulse echoes.

FIG. 2 represents two successive emission pulses $E_1$ and $E_2$ and echoes $R_1$, $R_2$, $R_3$, located respectively in reception windows $C_1$, $C_0$, $C_2$, synchronized on the pulse $E_1$ and corresponding to three areas of predetermined distances from the emissive surface of the probe 2. The area corresponding to $F_0$ is the one containing the focal spot having substantially an extended ellipsoid shape, the main axis of which coincides with the main axis of the generator 1; the area corresponding to $F_1$ is located on one side of the focal spot whereas the area corresponding to $F_2$ is located beyond it.

When an echo is detected in the window $F_2$, this means clearly that the target is located beyond the focus in the vertical direction and the generator must be moved upward to make coincide the focus with the target. Conversely, in case of detection of an echo in the window $F_1$, the generator must be moved downward.

The echo signals transmitted inside the duration of these gating pulses supplied by the generators 6 and 8, i.e. corresponding to echoes formed respectively in the areas $F_2$ and $F_1$, are respectively applied to circuits 19 and 20 which control the operation of the motor 21 in the appropriate direction in order to correct the vertical shifting of the target with respect to the focus by moving the generator 1.

When the target coincides with the central area $F_0$ which contains the focal spot, an echo is transmitted through the gate 10 and is set ON and transmits its output 1001 to trigger the shootings. However, this occurs only if the echo generator has been previously positioned in such a way that its axis crosses the target ($\theta = E$).

To this effect, a second input of the AND gates 12 and 13 is connected to the output of the gating pulse generator 7, whereas a third input is connected to either one or the other of two comparators 14 and 15 which are themselves connected to the circuit 206 which provides a numerical indication of the position $\theta$ of the scanning beam of the probe 2. When $\theta$ is inside the area $\Delta\theta + E$, the comparator 14 sends a logic level 1 to the gate 12, whereas the comparator 14 sends a logic level 1 to the gate 13 when $\theta$ is inside the area $\Delta\theta - E$. The value of $\Delta\theta$ varies from 0 to a maximum value which defines two angular approach areas of the target, whereas E is a fixed value which corresponds advantageously to half of the angle through which the focal spot of the generator 1 is seen from the center of the probe emissive surface.

The AND gates 12 and 13 are connected to two circuits 17 and 19 which control the operation of one or the other of the two motors 22, 23 respectively in one or the other direction. The motor 22 is controlled when a relay 220 sets up the connection between the circuits 17 and 18 and its control input 221. The motor 23 is controlled when a relay 230 sets up the connection between the circuits 17 and 18 and its control input 231. These two relays 220, 230 are controlled respectively by signals appearing at the respective outputs 2041 and 2042 of the device 204, i.e. when the scanning is carried out in the figure plane or respectively in the perpendicular plane.

The motor 22 thus rotates in one or the other direction in order to carry out a longitudinal displacement of the generator 1 in an appropriate direction for bringing its focal spot under the target.

As soon as the angular position information supplied by the circuit 206 moves outside the comparators area, the gates 12 and 13 are closed, thus resulting in the shut-off of the motor 22, which means that the focal spot is on the target in the longitudinal direction ($\theta = E$).

The motor 23 functions in the same way as motor 22 but effecting transversal displacement of the generator 1 in one direction or the other, thus drawing the focal spot on the target in the transversal direction. It is only when the coincidence is obtained both in the longitudinal direction and in the transversal direction that the device 206, which has been correctly positioned to this effect, will indicate that $\theta = E$ and will open the gate 41 in order to authorize the shooting.

It will be observed that the device of FIG. 1 defines, in the space containing the focal spot, two groups contained respectively in two orthogonal planes, of three areas, via a central area which tightly frames the focal spot in its small dimension, and two approach areas located on each side of the central area. In each one of the two orthogonal planes, three distance areas are defined. One centered on the top of the beam via a central area which tightly frames the focal spot in its large dimension and two approach areas located on each side of the central area.

The method disclosed enables the carrying out of a permanent automatic tracking of the target for triggering high accuracy shootings, provided that a rough positioning of the target be carried out previously be means of a visual localization process, preferably of the type described in the above-mentioned patent in order to draw the target inside the approach areas. This tracking will be advantageously carried on during the shootings, the triggering signal at the output 1001 corresponding for instance, to a logic level 1 as long as the target is reached, and the changing to a logic level 0 to stop the shootings when the target is out of the focal area.

The method is analyzed as a control of the simultaneous displacement of the power radiator and of the echographic probe as a function of the coordinates of the impact region of the echographic beam on the stationary target, the set values being the coordinates corresponding to a given position of the power radiator for which its focus is located on the target surface. Since the echographic probe moves at the same time as the power radiator, the coordinates of the impact region of the echographic beam on the target are linked in effect to the power radiator position. For any type of echographic scanning, the instantaneous coordinates can be determined from the echographic distance (which can be determined from the propagating time of the echoes) and from the echographic beam position (which is known since the scanning is under control).

The preferred embodiment described is a simple and efficient implementation.

Figure 3:
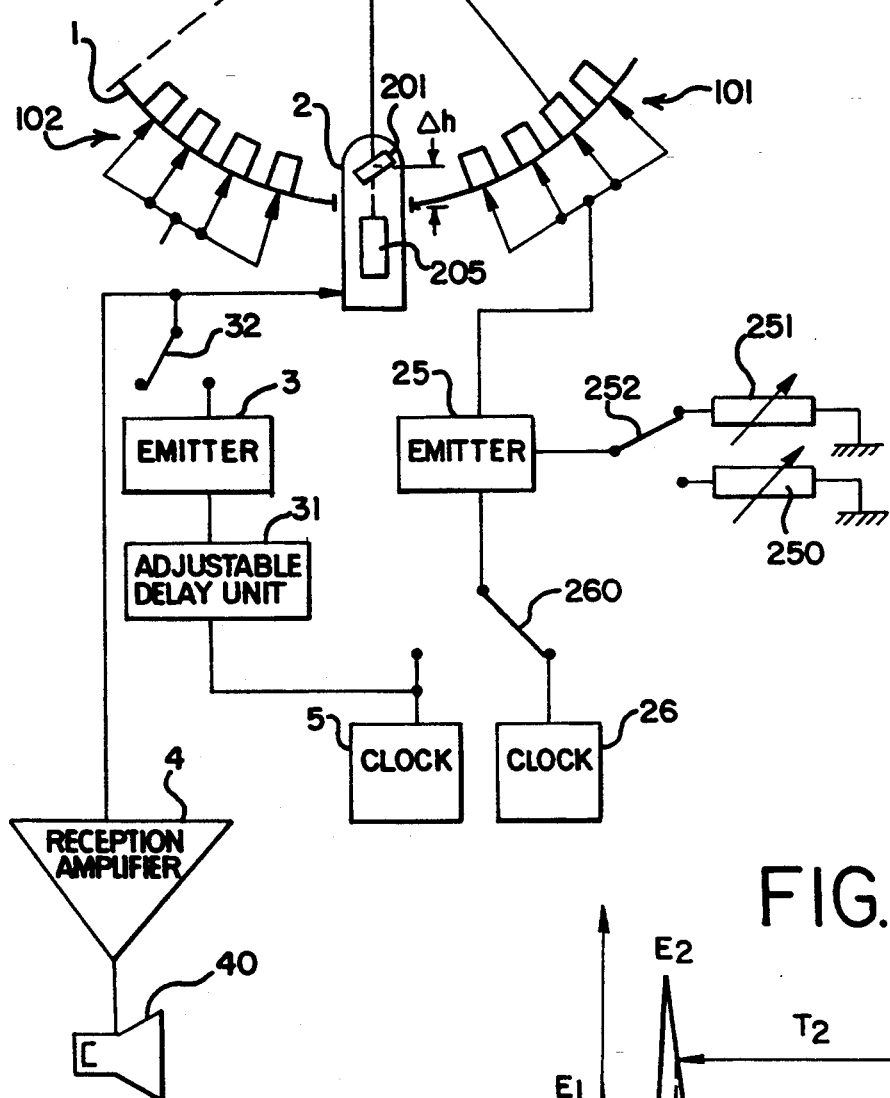
FIG. 3 is a block diagram of a visualization circuit of the focal spot.

FIG. 3 represents diagrammatically an additional circuit of the device of FIG. 1, provided for the visualization of the focal spot. In the same way as on FIG. 1, the synchronization of the echographic pulses is controlled by a clock 5, but an adjustable delay circuit 31 is inserted between the clock 5 and the emitter 3, and the emitter 3 is connected to the probe 2 through a switch 32, which enables the switching on or off of the echographic emission. In the same way as on figure 1, the receiving and image forming circuits have been represented symbolically in the form of a reception amplifier 4 which energizes the brilliance control electrode of the cathode ray tube 40. The emitter 25 represents the transducers of the power generator 1 in a purely symbolic manner that is well known.

The power of the emitter 25 is adjustable (for instance from 0.5 to 1 Kw as a peak value) by well known means, represented symbolically by two adjustable resistance 250-251 connected to a control input of the emitter 25 through a switch 252.

During the mode of operation described at present and which provides for the visualization of the focal spot, the emitter 25 is synchronized by the clock 5 (position 1 of the switch 260). It must be well understood that, for the treatment mode operation, the emitter 25 operates under non-reduced power (for instance at a peak value of 100 Kw). It is then synchronized by a clock 26 when the switch 260 is in position 2.

Figure 4:
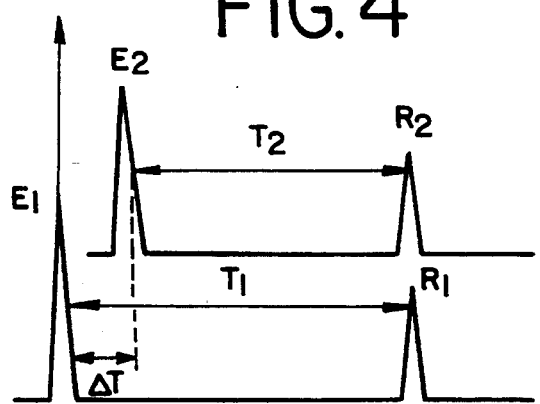
FIG. 4 is a diagram of the above-mentioned circuit depicting pulses and echoes.

When, as indicted on FIG. 3, the switch 260 is in position 1 (on) and the switch 252 is in one of the two (or of several) reduced power emission positions (for instance 251) the emitter 25 is synchronized to emit for instance 256 pulses during the 1/10th second interval which elapses normally between two shootings, and is used for the echography. These pulses (such as $E_1$ on FIG. 4) are reflected from the target, which has been previously localized, in such a way that one of its reflecting surfaces is located at the power radiator focus and the echoes $R_1$ thus formed, coming from a target region which coincides with the focal spot of the power radiator, are received by the probe 2 and supply an image of the said focal spot, as explained in the abovementioned patent. Since the beam is emitted by the fixed power radiator, the focal spot alone is clearly visible on this image.

On the device shown, it is possible to set simultaneously into operation the emitters 25 and 3. (by actuating simultaneously the switches 260 and 32). The probe 2 operates then as an echographic emitter as well as a receiver of the echoes resulting from the reflections of the beams simultaneously emitted by the probe and by the power radiator, with the result that the image of the focal spot appears in overbrightness on the image of the target and its environment formed by the probe. The adjustment of the power of the emitter 25 and thus of the power radiator, proportionally enables the respective brightness of the image of the focus of the treatment beam and the image of the target.

As shown on FIG. 3, the respective distances from the power radiator and from the echographic probe to the focus, differ by $\Delta h$, with the result that in (FIG. 4), the times $T_1$ and $T_2$ which elapse between the respective echoes ($R_1$ and $R_2$) and the corresponding emission pulses ($E_1$ and $E_2$) differ by an interval $\Delta T$ proportional to $\Delta h$. In order that the echoes $R_1$ and $R_2$ coincide in time, for obtaining the simultaneous formation of the two images, the delay supplied by the circuit 31 is adjusted to the value $\Delta T = \Delta h(1/c)$, c being the propagation speed.

Obviously several modifications can be brought to the devices described and represented, without departing from the scope of the invention.

It must be well understood that the processes and devices described are applicable to the hyperthermy as well as to the lithotripsy, or to any other treatment using focused elastic waves requiring the accurate echographic location of the target and/or the visualization of the focal spot of the generator of the treatment wave.

I claim:

1. A location and treatment device of an anatomic target object comprising:

a power generator with treatment focusing means for focusing a treatment beam of elastic treatment waves in a predetermined position, said treatment beam having an axis of symmetry and a focal point;

echographic scanning means including an ultrasonic transducer for generating an echographic beam, said echographic beam corresponding to a region of impact on the target object;

said ultrasonic transducer configured to scan a region of space occupied by the treatment beam;

echo receiver and image forming means, coupled to said ultrasonic transducer for forming an echographic image of the target object in real time from energy reflected from the target object during a treatment period;

display means coupled to said image forming means for displaying a mark representing the focal point of the treatment beam at the predetermined position;

displacement means linked both to said treatment focusing means and to said ultrasonic transducer for establishing a coincidence between the mark and the image of the target object;

said displacement means further including gating means for selecting echoes corresponding to the image of the target object and for generating as a function of the propagation time of the selected echoes and the angular position of the echographic beam with respect to the axis of symmetry of the treatment beam, deviation signals which correspond to coordinates defining the region of impact with respect to said ultrasonic transducer; and means for controlling said displacement means and responsive to said deviation signals, for stopping the operation of said displacement means once a coincidence between the mark and the image of the target object is reached, and for triggering said power generator for causing the emission of the treatment beam when said coincidence is reached.

2. A device as claimed in claim 1, wherein said scanning means includes a B-scanner having a probe, for producing said echographic beam which scans an angular sector having an axis of symmetry and means for rotating said probe of said B-scanner around the axis of symmetry of the treatment beam for successively scanning a first and a second orthogonal plane, said scanning producing echoes from energy of said echographic beam reflected from the target object.

3. A device as claimed in claim 2, wherein said gating means further includes means for effecting selection of said echoes in each of said first and second orthogonal planes as a function of the angular position of the axis of symmetry of the echographic beam with respect to the axis of symmetry of the treatment beam, and with respect to the distance between the impact region on the target object and the ultrasonic transducer.

4. A device as claimed in claim 3 wherein said gating means further includes first selection means for selecting and separating said echoes produced by the ultrasonic transducer returned from a first, a second, and a third impact region, said first impact region located at a first distance from the ultrasonic transducer, said second impact region located at a second distance from the ultrasonic transducer, and said third impact region located at a third distance from the ultrasonic transducer, wherein the second distance corresponds to the focal point of the treatment beam such that the first distance is shorter than the second distance and the third distance is longer than the second distance, where an angular position of the echographic beam is defined by an angle about equal to zero degrees;

second selection means for selecting and separating said echoes formed in said impact regions on the target located in each of said first and second orthogonal planes respectively, where an angular position of the echographic beam is defined by angles about equal to zero, greater that zero, and less than zero, respectively;, sensor means for supplying to said first and second selection means information relating to the angular position of the echographic beam;

said means for rotating said probe of said B-scanner is configured to bring said probe of said B-scanner at periodic time intervals into scanning positions corresponding to said two orthogonal planes;

said means for controlling said displacement means further including first control means for varying the angular position of the axis of symmetry of the echographic beam with respect to the axis of symmetry of the treatment beam, and second control means for varying the distance from said region of impact on the target object to the ultrasonic transducer.

5. A location and treatment device of an anatomic target object comprising:

an ultrasonic power generator with treatment focusing means for focusing a treatment beam of elastic pulsed waves at a focal region, said treatment beam having an axis of symmetry;

said treatment beam transmitted at a first predetermined rate at periodic intervals;

echographic means for locating said focal region, said echographic means further including an ultrasonic transmitter-receiver transducer for generating an echographic beam of echographic pulses and for receiving echoes, said echoes formed from the echographic pulses transmitted at a second predetermined rate which is substantially higher than said first predetermined rate;

scanning means coupled to said ultrasonic transmitter-receiver transducer for carrying out a plane scanning with said echographic beam in the region of the space occupied by said treatment beam;

a receiver and image forming means having a display, coupled to said ultrasonic transmitter-receiver transducer for forming on the display in real time, an echographic image of the target object from energy of the echographic beam reflected from the target object, said energy in the form of echoes reflected from the target during a treatment period;

said display adapted to form a mark representing the theoretical position of said focal region;

displacement means linked to both said treatment focusing means and said ultrasonic transmitter-receiver transducer for establishing the coincidence of the mark with the image of the target object; and triggering means for causing transmission by said power generator, during said periodic intervals and at said second predetermined rate, of a plurality of control pulses having a power level substantially lower than a power level of the treatment beam wherein the control pulses are transmitted simultaneously with the echographic pulses, such that energy from said control pulses and from said echographic pulses reflected from the target object are in the form of echographic echoes and secondary echoes, said echographic echoes and said secondary echoes being applied to said receiver and image forming means for forming an echographic image of the target and its environment wherein an image of the focal region appears as overbrightness relative to the image of the target object.

6. A device as claimed in claim 5 wherein the ultrasonic power generator and the ultrasonic transmitter-receiver transducer have respective transmitting surfaces separated from the focal region by a first and a second predetermined distance wherein said location and treatment device further includes delay means for delaying the echographic pulses with respect to the control pulses by a time interval proportional to the difference between the first and the second predetermined distances.

* * * * *

UNITED STATES PATENT AND TRADEMARK OFFICE
CERTIFICATE OF CORRECTION

PATENT NO. : 5,431,621

DATED : July 11, 1995

INVENTOR(S) : Dory

It is certified that error appears in the above-indentified patent and that said Letters Patent is hereby corrected as shown below:

On the title page, item [54] and Col. 1, line 2, after "PROCESS AND DEVICE" insert —OF LOCATION AND DESTRUCTION—.

Col. 1, line 12, "U.S. Pat. No. 4,658,858" should be --U.S. Pat. No. 4,658,828--.

Col. 7, line 48, after "for" delete "." .

Signed and Sealed this

Seventeenth Day of October, 1995

Attest:

BRUCE LEHMAN

*Attesting Officer*     *Commissioner of Patents and Trademarks*